(12) United States Patent
Walker et al.

(10) Patent No.: US 9,416,341 B2
(45) Date of Patent: Aug. 16, 2016

(54) SUSTAINED RELEASE ADDITIVES FOR FERMENTATION PRODUCTS

(75) Inventors: Teresa L. Walker, Clovis, CA (US); Lars Petersen, Fresno, CA (US); Robert H. Menzies, Waupaca, WI (US)

(73) Assignee: Gusmer Enterprises, Inc., Waupaca, WI (US)

( * ) Notice: Subject to any disclaimer, the term of this patent is extended or adjusted under 35 U.S.C. 154(b) by 2953 days.

(21) Appl. No.: 11/688,543

(22) Filed: Mar. 20, 2007

(65) Prior Publication Data

US 2007/0218133 A1    Sep. 20, 2007

Related U.S. Application Data

(60) Provisional application No. 60/784,091, filed on Mar. 20, 2006.

(51) Int. Cl.
| | |
|---|---|
| *A61K 9/22* | (2006.01) |
| *C12G 1/04* | (2006.01) |
| *C12G 1/022* | (2006.01) |
| *C12H 1/14* | (2006.01) |
| *C12M 1/00* | (2006.01) |

(52) U.S. Cl.
CPC ............... *C12G 1/04* (2013.01); *C12G 1/0203* (2013.01); *C12H 1/14* (2013.01); *C12M 29/00* (2013.01); *Y02E 50/17* (2013.01)

(58) Field of Classification Search
CPC ....... C12G 1/0203; C12G 1/04; C12M 29/00; C12H 1/14
USPC .......................... 426/11, 592; 424/468; 435/41
See application file for complete search history.

(56) References Cited

U.S. PATENT DOCUMENTS

| | | | |
|---|---|---|---|
| 3,133,862 A | 5/1964 | Wershaw et al. | |
| 3,545,978 A | 12/1970 | Agabaliants | |
| 4,178,389 A | 12/1979 | Pilla | |
| 4,282,255 A | 8/1981 | Sandine et al. | |
| 4,690,682 A | 9/1987 | Lim | |
| 4,822,534 A | 4/1989 | Lencki et al. | |
| 6,627,238 B1 * | 9/2003 | Kim et al. | 426/94 |
| 6,841,515 B2 | 1/2005 | Burnham | |
| 2002/0172738 A1 * | 11/2002 | Young, III | 426/15 |
| 2004/0115307 A1 | 6/2004 | Boyd | |
| 2004/0146601 A1 | 7/2004 | Oszlanyi et al. | |

FOREIGN PATENT DOCUMENTS

| | | |
|---|---|---|
| EP | 1 195 160 A1 | 4/2002 |
| WO | WO 99/61646 | 12/1999 |
| WO | WO 2004/037004 | 5/2004 |

OTHER PUBLICATIONS

Chaudhari, D., Controlled drug delivery systems. Literature Seminar—University of Alabama (2004).
Kaparissides, C., S. Alexandridou, K. Kotti, and S. Chaitidou. Recent advances in novel drug delivery systems. AZojono—Journal of Nanotechnology Online. 2:1-11 (2006).
Vogelson, C.T. Advances in drug delivery systems. Modern Drug Discovery. 4(4):49-50, 52 (2001).
Chaney, D., S. Rodriguez, K. Fugelsang, and R. Thornton. Managing high-density commercial scale wine fermentations. J. Appl. Micro. 100:689-698, vol. 2 (2006).
Alfenore, S., C. Molina-Jouve, and S.E. Guillouet. Improving ethanol production and viability of *Saccharomyces cerevisiae* by a vitamin feeding strategy during fed-batch process. Appl. Microbiol. Biotechnol. 60:67-72 (2002).
Butzke, C.E. Survey of yeast assimilable nitrogen status in musts from California, Oregon, and Washington. Am. J. Enol. Vitic. 49:220-224 (1998).
Ingledew, W.M. and R. Kunkee. Factors influencing sluggish fermentations of grape juice. Am. J. Enol. Vitic. 36:65-76 (1985).
Julien, A., J.L. Roustan, L. Dulau, and J.M. Sablayrolles. Comparison of nitrogen and oxygen demands of enological yeasts: technological consequences. Am. J. Enol. Vitic. 51:215-222 (2002).
Manginot, C., J.L. Roustan, J.M. Sablayrolles. Nitrogen demand of different yeast strains during alcoholic fermentation. Importance of the stationary phase. Enzyme and Microbial Technology. 23:511-517 (1998).
Ough, C.F., M. Davenport, and K. Joseph. Effects of certain vitamins on growth and fermentation rate of several commercial active dry wine yeasts. Am. J. Enol. Vitic. 40:208-213 (1989).
Sablayrolles, J.M., C. Dubois, C. Manginot, J.L. Roustan, and P. Barre. Effectiveness of combined ammoniacal nitrogen and oxygen additions for completion of sluggish and stuck wine fermentations. Journal of Fermentation and Bioengineering. 82:377-381 (1996).

* cited by examiner

*Primary Examiner* — Vera Stulii
(74) *Attorney, Agent, or Firm* — Daniel A. Blasiole; Charles S. Sara, Esq.; DeWitt Ross & Stevens SC (57) ABSTRACT

A sustained release delivery system and composition of materials for slowly releasing an additive to a fermentation fluid over a sustained period of time of up to 96 hours is described. The product of the present invention includes a complement of additives and a sustained release mechanism to allow a single addition of components that yield release profiles consistent with multiple additions in juice, fermented beverages, other foodstuffs, and biofuels production.

28 Claims, 3 Drawing Sheets

SUSTAINED RELEASE ADDITIVES FOR FERMENTATION PRODUCTS

CROSS-REFERENCE TO RELATED APPLICATION

This application claims priority under 35 U.S.C. §119(e) to U.S. Provisional Patent Application 60/784,091 filed Mar. 20, 2006, the entirety of which is incorporated by reference herein.

FIELD OF THE INVENTION

The present invention relates generally to enhancing the fermentation process of food products by providing additives to microbes over time allowing release of essential components during specific stages of growth that will assist in vital metabolic processes. More particularly, this invention relates to enhancing and manipulating the alcoholic fermentation of microbes in juice, fermented beverages, other foodstuffs, and biofuels production.

CITED REFERENCES

A full bibliographic citation of the references cited in this application can be found in the section preceding the claims.

BACKGROUND OF THE INVENTION

While the earliest accounts in medicine date back to ancient civilizations, more recent scientific discoveries have fueled the progression of delivery system technologies. In 1862, John Wyeth, a pharmacist and researcher, manufactured medicines in large quantities for doctors and wholesale distribution. His commitment to the mass production of medicines led to the development of the 'compressed pill' or tablet and the invention of the rotary tablet press in 1872. Pharmaceuticals dispensed in tablet form allowed convenience in taking medication but still often required multiple administrations. The continued development of the modern pharmaceutical industry, especially since the 1950s, has led to a plethora of controlled release or time release technologies. These technologies have been used with numerous pharmaceuticals and can be divided into three categories—delayed release, site directed systems, and sustained or time release (Chaudhari, 2004).

Delayed release systems dispense repetitive doses of one or more active ingredients often utilizing parenteral release routes. These release routes include transdermal drug delivery, intravenous injections, intramuscular injections, or subcutaneous implants. Transdermal drug delivery systems are generally non-invasive, are aesthetically acceptable, can provide local delivery over several days, and can be used on unconscious patients (Kaparissides et al., 2006).

Site directed technologies are utilized in numerous biological systems to deliver active ingredients directly to targeted locations. Historically, these systems have been diffusion controlled; however, modern research is investigating biodegradable polymer systems (Vogelson, 2001). Targeted delivery systems include polymeric microspheres, microcapsules, nanocapsules, macromolecular complexes, and polymeric beads.

Sustained release systems are formulated to dissolve slowly and release a substance over time. These systems are generally formulated with an active substance embedded into a matrix of time release agents. These sustained release mechanisms allow active ingredients to escape through diffusion or through osmotic release, i.e., physical swelling to form a gel in which active ingredients are released through the surface of the product.

With the success of advanced delivery technologies, scientists have expanded the industry beyond pharmaceuticals to include various applications involved with agriculture and bioremediation. BIOCAPSULES (Center of Bioremediation, Salt Lake City, Utah) offer site-specific encapsulated microorganisms for sustained, delayed, and/or targeted release in environmental and bioremediation applications (http://programs.weber.edu/bioremediation/biocapsu.htm). The focus of BIOCAPSULES is to provide stable, simultaneous time release of microorganisms and key nutrients to environmental applications using a biodegradable matrix. Reference is also made to a product called BIOGREEN (Biogreen$_{LTD}$, Melbourne, Vic, Australia) for sustained release insecticides in crop control. U.S. Pat. No. 5,472,955 to Kellerby is directed to sustained release insecticides for horn fly control. Further, a product called MICROESSENTIALS EZ (Cargill AgHorizons, Cargill Limited, Winnipeg, Manitoba, Canada) is directed to sustained release fertilizers for crop nutrition.

While sustained or time release technologies have not yet been utilized in fermentation applications, research has shown that balanced nutrition is extremely important to fermentation rate, cell growth, and fermentation kinetics (Chaney et al., 2006). Winemakers often are required to add additives at various stages of the fermentation to prevent stuck fermentations, to reduce or prevent formation of hydrogen sulfide, acetic acid, ethyl carbamate, and other unwanted metabolites as well as to improve aroma and flavor profiles.

The role of microbial supplementation via complex additives and nutrients containing assimilable nitrogen, vitamins, minerals, and amino acids has been well documented (Agenbach, 1977; Butzke, 1998; Ingledew and Kunkee, 1985; Ough et al., 1989; and Sablayrolles, et al., 1996). Research has shown that multiple additions are indeed superior to single additions (Alfenore et al., 2002; Chaney et al., 2006; Julien et al., 2000; and Manginot et al., 1998). Research suggests that adding all nutrient supplements simultaneously can lead to a rushed fermentation rate, an imbalance in uptake and usage of nitrogen compounds, and less fruity character of wines.

Addition of nitrogen to deficient juices is extremely important for cell growth, metabolism, protein synthesis, and alcohol resistance; however, the timing of the addition is equally as important. For instance, one large addition of diammonium phosphate initially can delay or inhibit the uptake of amino acids. Therefore, multiple additions over time are preferred and will keep the fermentation process at its peak increasing the reliability of the fermentation. Chaney et al. 2006 reported Shiraz grapes that received two nitrogen additions completed fermentation with low volatile acidity at standard temperature (29° C.); whereas, duplicate tanks with the standard nitrogen addition regime produced increased volatile acidity and failed to complete fermentation. Additive supplementation should be completed during the first half of fermentation.

Most winemakers do not have the option of performing multiple additions due to the volume of wine produced and time constraints during harvest.

SUMMARY OF THE INVENTION

The present invention is directed to a composition for the sustained release of additives in a fermentation fluid comprising a gelling agent, at least one additive, and a binder, wherein the gelling agent and the binder are present in effective amounts to allow the sustained release of the at least one additive in the fermentation fluid for a period of at least 12 hours.

The present invention is further directed to sustained release nutrient system for a fermentation fluid comprising a gelling agent, selected from the group consisting of alginate, a nutritionally effective amount of at least one nutrient, a calcium source; and a binder, wherein the gelling agent and the binder are present in effective amounts sufficient to allow the sustained release of the at least one nutrient in the fermentation fluid for a period of at least 12 hours.

The present invention is further directed to a method of preparing a sustained release tablet for fermentation fluids comprising forming a binder composition by mixing about 35 to about 75% by weight of an additive in a gelling agent, adding between about 0.2% and 2% by weight of a firming agent to the binder composition to increase the density in order to assure that the sustained release tablet remains in the fermentation fluid; adding a lubricant to the binder composition in amounts ranging between about 0.25 and 2% by weight; and mixing in between about 0.25% and 2% by weight of a disintegrating agent to the binder composition and forming a tablet for adding to the fermentation fluid to release the additive for a period of time up to 96 hours.

The invention is a sustained release delivery system and composition of materials to manipulate microbial activity in a fermentation fluid or liquid. The preferred invention is directed to the use of a sustained release nutrient supplement to manipulate alcoholic fermentation in wine. Furthermore, the invention is directed to methods of producing a sustained release nutrient.

The product of the present invention consists of complex additives and nutrients and a sustained release mechanism to allow a single addition of components that yield release profiles consistent with multiple additions in juice, fermented beverages, other foodstuffs, and biofuels production. Preferably, the additive product is compressed into tablets which will slowly dissolve and simulate multiple administrations of the nutrient components. Alternate terminology for tablets includes but is not limited to wafers, pellets, ropes, bricks, etc.

The sustained release mechanism will assist users with additive addition. The product could be a single tablet or a multi-tablet system designed to supply key nutrients to microbes initially and throughout the fermentation cycle. In a multi-tablet system, different ratios of the sustained release mechanism can be utilized to allow release when most advantageous to the fermentation. The sustained release system will slowly dissolve over a few days releasing key nutrient components necessary to sustain, enhance, and manipulate microbial activity.

Advantageously, the product will allow the convenience of a one-time addition of additive tablets which have built-in sustained release functionality.

A key benefit of this invention is "ease of use." With this time-delivered additive product, "release profiles" are created where different nutritional components are released at different times or in different ratios. Ideally, the release rate will take place over two to five days in aqueous solution at room temperature in low pH. Additional benefits include enhanced, healthy fermentations via nutritional components that promote growth, viability, and long-term survival; reduced stuck or sluggish fermentations; increased alcohol tolerance; and balanced amino acid uptake resulting in wines with better aromas and flavors.

The invention consists of components designed to supplement specific stages during fermentation. As an example, it is best to add less diammonium phosphate initially and more diammonium phosphate after the fermentation is active.

Due to the sustained release functionally of the present invention, winemakers can add these nutritional supplements once at the beginning of fermentation thus achieving the benefit of multiple administrations. In contrast to the prior art, this invention has a sustained release function to allow components to be released at various stages thus performing multiple additions. The nutrient supplementation of the present invention can be manufactured cost effectively and has a broad range of potential usage in food, fermented beverages, and biofuel production.

The objects and advantages of the invention will appear more fully from the following detailed description of the preferred embodiment of the invention made in conjunction with the accompanying drawings.

DETAILED DESCRIPTION OF THE INVENTION

As used in this disclosure, the term 'additive' generally refers to any substance added in relatively small amounts to another product, in this case the fermentation fluid, to improve, strengthen, or otherwise alter the fluid. In the present invention, additives are typically nutrients which provide a source of nourishment to the fluid.

While additives are often added to fermentation products, such as juice, food, and biofuels fermentations, they do not provide a sustained release mechanism that allows slow diffusion into the product over extended periods of time. The present invention provides a sustained delivery system to enhance and manipulate the fermentation of juice, beverages, other foodstuffs, and biofuels production, otherwise known as "fermentation fluids" or "fermentation liquids." This invention relates to a sustained release mechanism that can provide a stable, efficient, reliable fermentation through the measured release of additive components at key stages during the fermentation process without the requirement of manually adding the additives at measured increments during the fermentation process.

The sustained or controlled release system of the current invention supplies time release functionality through a blend of specific components including but not limited to a gelling agent, a binder and at least one additive in a quantity sufficient to allow the sustained release of the additive into the fermentation product for periods up to and extending beyond 96 hours without the requirement of replenishing the additive. In its simplest form a sustained release additive for fermentation is formed of a tablet with a combination of a gelling agent, such as alginate, a calcium source, and an additive source, typically a nutrient such as a nitrogen source, with a 48 hour sustained release.

Gelling Agent:

The gelling agent is intended for the controlled delivery and release of the additives to the fermentation system and to maintain the proper proportion of the additive in the fermentation product over an extended period of time. Gelling agents for this purpose are known to the art. A controlled release, timed release or disintegration agent can be defined as a substance or mixture of substances added to a composition to facilitate its breakup or disintegration after administration into the fermentation fluid. The use of the gelling agent in this invention provides for a controlled breakdown and distribution of the additives in the fermentation fluid. Small, but important levels of a conventional disintegrant, such as microcrystalline cellulose, can be added to further refine and regulate the rate of tablet disintegration in the fermentation fluid.

Examples of delivery systems include but are not limited to alginates, hydrocolloids, such as carrageenan, agar, gelatin and pectin, and gums, e.g., guar gum, gum arabic, locust bean gun, xanthan gum and gelatin gums, cellulose derivatives, e.g., ethyl cellulose and hydroxylpropyl methylcellulose, maltodextrin, and food starches, e.g., corn, wheat, rice, potato and tapioca, and non-water soluble coatings, e.g., waxes, zeins, fatty acids, shellac, and edible oils.

Alginates are the most preferred delivery system. Alginates have gel-forming properties that create the sustained release profile. Examples of alginates include sodium alginate, potassium alginate, calcium alginate, magnesium alginate, ammonium alginate, and triethanolamine alginate. A preferred alginate is sodium alginate (PROTANAL LF200M (FMC BioPolymer, Drammen, Norway). Alginates are present in the formula in amounts ranging from 0 to 20% by weight, preferably in amounts ranging from 2 to 8% by weight, and most preferably about 4% by weight. The gelling agent, which on contact with the fermentation fluid, forms a matrix structure that releases the additive in a controlled manner. The concept of using gelatin to enclose both liquid (i.e. cod liver oil, vitamin E) and powder substances is known to the art. Reference is made to L. Lachman, et al., 1971; Porter, 1990; and Tyle, 1990 for non-limiting examples of suitable delivery systems.

Binders and Excipients:

A dense inert substance may be added to the composition to increase the density in order to assure the sustained release tablet remains in the fermentation fluid. The filler material which may be employed in the process of the instant invention is preferably relatively water insoluble and can be chosen from any well known in the art, such as tableting agents, tablet anti-adherents, tablet binders, tablet direct compression excipients, talc, calcium carbonate, colloidal anhydrous silica, sodium starch glycolate or mixtures thereof. A calcium source is the preferred firming agent in food and has the added advantage of dissolvability, high calcium content, and no off-aroma or flavors. Further, calcium binds with the gelling agents to form stronger gelling networks. Examples of calcium sources include: calcium chloride, calcium citrate, calcium phosphate, calcium carbonate, calcium lactate, calcium aspartate, calcium stearate, and calcium sulfate. A preferred calcium source is tri-calcium citrate (Gadot Bio-chem (USA) Inc., Syosset, N.Y.). The calcium source is present in the formula in amounts ranging from 0 to 20% by weight, preferably in amounts ranging from 0.25 to 5% by weight, and most preferably about 1% by weight.

The present invention can also comprise any other suitable ingredient well known to those skilled in the art, such as adsorbents, antioxidants, buffering agents, colorants, flavorants, sweetening agents, lubricants, diluents, tablet disintegrants, tablet glidants, polishing agents, and other equivalent excipients selected from the group consisting of magnesium stearate, calcium stearate, zinc stearate, powdered stearic acid, hydrogenated vegetable oils, polyethylene glycol, mineral oil, an FD&C color, modified cellulose, lactose, polyethylene glycol, colloidal silicon dioxide, talc, sodium lauryl sulfate, quaternary ammonium salts, mannitol, sodium chloride, sodium sulfate, sodium phosphate, magnesium chloride, magnesium sulfate, magnesium phosphate, lactose, sucrose, glucose, polyethylene glycols, waxes, hydrogenated castor oil, starch, polyvinyl pyrrolidone ad a combination thereof. Non-limiting examples of binders and fillers include TABULOS and CAB-O-SIL M5 (Cabot Corporation, Tuscola, Ill.).

The addition of the proper lubricant is highly desirable as it improves the rate of flow of the tablet granulation, prevents adhesion of the tablet to the surface of the tablet presses, reduces interparticle friction and facilitates the ejection of the tablet from the press cavity. The lubricant employed in the composition of the present invention can be any of the more common lubricants known in the art such as, for example, magnesium stearate, sodium stearate, calcium stearate, and stearic acid. The lubricant is present in the formula in amounts ranging from 0 to 10% by weight, preferably in amounts ranging from 0.25 to 2% by weight, and most preferably about 0.6% by weight. Magnesium stearate is the preferred lubricating agent. A preferred source of magnesium stearate is Vivion Inc. (San Carlos, Calif.).

Silicon dioxide is used as a free-flowing agent. Silicon dioxide is present in the formula in amounts ranging from 0 to 10% by weight, preferably in amounts ranging from 0.25 to 2% by weight, and most preferably about 0.6% by weight. A preferred source of silicon dioxide is Vivion Inc. (San Carlos, Calif.).

Microcrystalline cellulose is used as a binding agent due to its excellent compression properties. Microcrystalline cellulose also has lubrication and disintegration properties. Microcrystalline cellulose is present in the formula in amounts ranging from 0 to 80% by weight, preferably in amounts ranging from 10 to 35% by weight, and most preferably about 20% by weight. A preferred microcrystalline cellulose is AVICEL (FMC BioPolymer, Philadelphia, Pa.).

Additives:

The composition of the present invention provides a carrier for administering at least one additive for the fermentation product. In the wine industry, the additives are typically nutrients which are added to prevent stuck fermentations, to reduce or prevent formation of hydrogen sulfide, acetic acid, ethyl carbamate, and other unwanted metabolites as well as to improve aroma and flavor profiles. Typical nutrients include a nitrogen source, vitamins, minerals, yeast and yeast extracts, and others. The types and quantities of nutrients depend upon the fermentation product. Reference is made to the following non-limiting list for nutrients adaptable for the sustained release system of the present invention with respect to the wine industry. It is within the scope of the present invention to use the sustained release system for the release of other additives in other fluids depending on the needs of the fluid. For example, biofuels require specialized additives in their fermentation process. While the additives may be changed, the time release system of the present invention can be used to administer the additives.

Nitrogen is an essential element needed to avoid stuck and sluggish fermentations. Examples of nitrogen sources include: ammonium, ammonia gas, diammonium phosphate, diammonium sulfate, nitrite, nitrate, proteins, amino acids, and urea. A preferred nitrogen source is diammonium phosphate: (American Tartaric Products, Larchmont, N.Y.). Diammonium phosphate is an inorganic nitrogen source used in fermentations to promote yeast growth and aid in fermentation completion. Diammonium phosphate is present in the formula in amounts ranging from 0 to 25% by weight, preferably in amounts ranging from 0.5 to 8% by weight, and most preferably about 1% by weight.

Table 1 refers to the importance and usefulness of the vitamins and minerals:

TABLE 1

Additives (vitamins/minerals) and functional roles for yeast and bacteria metabolism.

| | Metabolic Function |
|---|---|
| Vitamin | |
| Biotin | Carboxylation and decarboxylation reactions |
| | Better kinetics and synergistic effect with nitrogen. |
| Calcium Pantothenate (vitamin B5) | Influences viability and fermentation rate |
| | Increased PA and increased YAN lead to decreased hydrogen sulfide. |
| Cobalamin (vitamin B12) | Promotes growth |
| Folic Acid (folate) | Production and maintenance of new cells |
| Inositol | Used for cell division and stimulating yeast growth rates |
| | Essential for membrane phospholipids synthesis |
| | Deficiency will decrease rate of carbohydrate metabolism. |
| Niacin (vitamin B3) | Coenzymes in oxidation/reduction reactions (under anaerobiosis) |
| Pyridoxine (vitamin B6) | Amino acid metabolism, deamination, decarboxylation |
| Riboflavin (vitamin B2) | As coenzymes in oxidation/reduction reactions (under anaerobiosis) |
| Thiamin (vitamin B1) | Increases cell viability |
| | Diminishes concentration of ketonic acids |
| | Essential element of carboxylase which assures decarboxylation of pyruvic acid into ethanol |
| | Improves sulfur dioxide equilibrium |
| Minerals | |
| Chromium | Involved in carbon fixation |
| Magnesium | Involved in cell integrity |
| | Plays a key role in metabolic control, growth and cell proliferation |
| | Limited Mg is responsible for decreased yeast growth and fermentative activity |
| | Better alcohol, temperature and osmotic resistance |
| | Higher ethanol yield |
| Manganese | Synergic effect with zinc, shorter generation time |
| Molybdenum | Involved in nitrogen fixation |
| Potassium | Required for yeast growth and fermentation |
| | Ions are necessary for phosphate uptake. |
| Zinc | Cofactor of glycolysis enzymes, increases alcohol tolerance, regulation of by-products (esters, alcohols, fatty acids) | formula in amounts ranging from 0 to 90% by weight, preferably in amounts ranging from 35 to 75% by weight, and most preferably about 69% by weight.

Yeast extract supplies amino acids, fatty acids, nucleic acids, vitamins and minerals to facilitate fermentation. Yeast extract is present in the formula in amounts ranging from 0 to 50% by weight, preferably in amounts ranging from 5 to 30% by weight, and most preferably about 5% by weight. A preferred yeast extract source is TASTONE 154 (Sensient Technologies, Milwaukee, Wis.). Other examples of yeast extract from Sensient Technologies include AX965, FM957, TT900, and AX1003. Examples of yeast extract from Lallemand (Montréal, Québec) include Fermaid 2133, FNI100, FNI 200, FNI 205, FNI 300, FNI 405.

Non-limiting examples of vitamins and minerals used in the formulations include biotin, chromium, cobalamin (B12), folic acid (B9), inositol, magnesium, manganese, molybdenum, niacin (B3), pantothenic acid (B5), potassium, pyridoxine (B6), riboflavin (B2), thiamin (B1), and zinc. A preferred source of vitamins and minerals is Micro-Essentials Trace ("MET") (Gusmer Enterprises, Fresno, Calif.), a pure vitamin and mineral blend. The vitamin/mineral blend is present While the sustained release system of the present invention can be used in the form of powders, the preferred embodiment is in the form of tablets, which are produced using a tablet press. In another embodiment, the additive blend could be processed by using an extruder, a fluidized bed dryer/coating process, or via microencapsulation to obtain different shaped products (pellets, ropes, wafers, bricks, etc.) with sustained release functionality.

The size of the tablets has been found to add to the sustainability of the release of the additives within the system. After much research, it was found that tablets produced in standard smaller tableting machines have rapid disintegration rates (<12 hours) compared to the products of the present invention. Without wishing to be held to one premise, it is believed that the longer disintegration rates of the present invention are due to the larger-sized tablets, i.e., tablets at least about 0.69-inch thick and 1.5-inches in diameter. This larger size in combination with the gelling agent contributes to a stronger gelling network.

The active ingredients and excipients are blended in appropriate amounts prior to dry granulation. The excipients help powders become more fluid, bulk up the tablet, or help powders fuse or link particles to one another. After ingredients are blended, the dry granulation process is used to form granules without using a liquid solution. These powders are compacted and compressed by techniques well known in the industry. Conventional tablet machinery and procedures, that is both direct compression and granulation, i.e., slugging, before compression, can be utilized. Those individuals involved in pharmaceutical and nutraceutical solid dosage form production are versed in the processes and the machinery used as the dosage form is a very common dosage form in the industry. An example of a suitable press is a STOKES R4 press equipped with a stainless steel, concave, bevel-edge die with 1.5-inch diameter.

The quantity of sustained-release additive added to the fermentation fluid depends on a number of factors including, but not limited to, the type of fermentation fluid, the type of additive, the purpose of the nutrition, the size of the sustained release tablet, the amount of gelling agent within the tablet, and the length of time of projected sustained release of the additives. The ultimate purpose of the sustain-release system of the present invention is to add the additive in a carrier which will activate a sustained release of the additive over a period of time in excess of normal or typical administration of the additive. Ideally, the system of the present invention should enable a sustained release of the additive over a period of 12 hours or more, preferably 24-48 hours, and more preferably greater than 96 hours.

The administration can be accomplished by one large tablet or bolus or by several smaller tablets all added simultaneously as long as the ultimate goal of sustained release is achieved. As an example, a sustained release inoculation in a fermentation fluid, such as wine, can be achieve at dosages ranging between 3 and 8 lbs/1000 gallons (G.) in fewer larger tablets or in several, e.g., 60 to 160 smaller tablets per 1000 G.

The final product comprises a mixture of a nutritionally effective amount of a additive, a gelling agent, a binder, a lubricant, and preferably microcrystalline cellulose, compressed into a tablet. The tablet provides for a sustained release of the nutritionally effective amount of the additive having a predictable and controllable release pattern. The tablet typically weighs from about 2 to about 40 grams and has a density of about 1.4 to 5.5. Preferably, the tablet weighs from about 5 to about 30 grams and has a density of about 1.5 to 3.0. The density of the tablet will allow it to remain in the fermentation fluid to release the additives for a period of time up to 96 hours in a predictable, controllable pattern. The product has advantages over the prior art in that less frequent administrations of the additives are required thereby reducing labor costs.

Although the invention was initially designed for use with the addition of additives to wine microbes during the fermentation process, it can be applied in other foods, fermented beverages, and biofuels areas. Non-limiting examples of other applications include juice, wine and beer.

Several alternate forms of the invention incorporating sustained release mechanisms could and may include targeted deliverable ingredients, processing aids, delivery systems and methods.

Examples of targeted deliverable ingredients and processing aids include but are not limited to enzymes including lysozyme, preservatives including sulfur dioxide, living organisms including bacteria and yeast, and clarification agents.

Examples of methods include but are not limited to the addition of sustained delivery systems to active ingredient blends prior to tablet formation, encapsulation or coating the exterior of the additive powder with wax or zein, or a combination of internal and external sustained release components incorporated into the active ingredient to form a slow dissolving sustained release agent. The concepts of encapsulation and micro-encapsulation are known to the art. Encapsulation involves enclosing medicines or ingredients in a usable form. Micro-encapsulation is a process that deposits tiny particles or droplets onto a solid dosage form (i.e. tablet, pellet, granule, or core) creating a shell, coating, or membrane around the active ingredient. The concept of coating the exterior of products is known to the art. Coating places a uniform layer of material on or around a solid dosage form. Coating is typically accomplished through one of four major techniques: sugar coating, film coating, micro-encapsulation, or compression coating. (Lachman, et al., 1986; Lakkis, 2007; Shelke, 2005; U.S. Department of Health and Human Services, 1997).

Combining the formula's ingredients synergistically improves the benefit and effect of the individual ingredients. The phrase "a nutritionally effective amount" means the amount of the composition that provides a benefit or improvement in the fermentation fluid over the sustained release process of the present invention.

The formula is preferably provided in the form of tablets. Non-limiting examples of formulations for the sustained-release product of the present invention are as follows:

Micro-Essentials Complete-Time Release ("MEC-TR") (Gusmer Enterprises, Fresno, Calif.) is a unique complete nutrient blend in tablet form with a sustained release system. This product contains yeast extract, yeast hulls, hydrolyzed casein, diammonium phosphate, vitamins and minerals, alginate, tri-calcium citrate, and excipients, according to the following formula:

| FORMULA EXAMPLE | | |
|---|---|---|
| INGREDIENT | % BY WT. | OTHER INFORMATION |
| Yeast extract | 14 | TASTONE 154 |
| Yeast hull | 7.5 | Nutrex 370 |
| Hydrolyzed casein | 5.7 | HCA-411 |
| Diammonium phosphate | 43 | DAP |
| Sodium alginate | 4 | PROTANAL LF200M |
| Tri-calcium citrate | 1 | |
| Vitamins and minerals | 2.8 | Micro-Essentials Trace |
| TABLETING | | |
| MCC and excipients | 22 | Microcrystalline cellulose, magnesium stearate and silicon dioxide |

The above formula is used in fermentations at the time of yeast inoculation at dosage ranging between 3-8 lbs/1000 G (approximately 60 to 160 tablets per 1000 G). Since MEC-TR is designed to minimize nutritional stress by supplying nitrogen sources, vitamins, and minerals associated with deficient juices/musts, the dosage rate is dependent on level of additive depletion. Each tablet weighs 20-26 g.

Micro-Essentials Boost-Time Release ("MEB-TR") is a unique complex nutrient blend in tablet form with a sustained release system. This product contains yeast extract, diammonium phosphate, vitamins and minerals, alginate, tri-calcium citrate, and excipients, according to the following formula:

| FORMULA EXAMPLE | | |
|---|---|---|
| INGREDIENT | % BY WT. | OTHER INFORMATION |
| Yeast extract | 5 | TASTONE 154 |
| Diammonium phosphate | 69 | DAP |

-continued

| FORMULA EXAMPLE | | |
|---|---|---|
| INGREDIENT | % BY WT. | OTHER INFORMATION |
| Sodium alginate | 4 | PROTANAL LF200M |
| Tri-calcium citrate | 1 | |
| Vitamins and minerals | 1 | Micro-Essentials Trace |
| TABLETING | | |
| MCC and excipients | 20 | Microcrystalline cellulose magnesium stearate and silicon dioxide |

The above formula is used in fermentations at the time of yeast inoculation at dosage ranging between 3-8 lbs/1000 G (approximately 60 to 160 tablets per 1000 G). Since MEB-TR is designed to minimize stress associated with nutrient deficient juices/musts, dosage rate is dependent on level of nutrient depletion. Each tablet weighs 20-26 g.

The following laboratory and commercial winery examples are provided to demonstrate the performance of the sustained release mechanism and to express the importance of multiple administrations of nutrients throughout the fermentation process as related to the present invention. The examples and illustrations are in no way intended to restrict the scope of the invention. Winemakers added products with sustained release systems initially at the onset of fermentation, and products without sustained release were added initially and multiple times throughout fermentation. The following acronyms apply throughout the examples:

MEC-TR: Micro-Essentials Complete-TR (Gusmer Enterprises, Fresno, Calif.)

MEP: Micro-Essentials Powder (Gusmer Enterprises, Fresno, Calif.)

MEB-TR: Micro-Essentials Boost-TR (Gusmer Enterprises, Fresno, Calif.)

EXAMPLE 1

The objective of this example was to show similar fermentation profiles for MEC-TR compared to MEP and MEP-multi addition. MEP was added to fermentations by two methods: 1) All MEP was added initially at onset of fermentation and 2) For MEP-multi addition, half of the powder was added initially and the other half of the powder was added 48-72 hours after onset of fermentation. Multiple administrations of MEP were used to evaluate the effectiveness of the sustained release system incorporated into the MEC-TR tablet. Our goal was to provide a sustained release system (added at onset of fermentation) that performs similar to powder added in multiple steps throughout the fermentation.

Frozen Chardonnay juice (Arroyo Seco Vineyards, San Martin, Calif.) was thawed and brought to room temperature before separating into 3 L treatment lots. MEP, MEP-multi addition and MEC-TR were utilized in this experiment.

Active ingredients and excipients were blended thoroughly before being compressed into tablets and then added to the juice as MEC-TR. MEC-TR contains a sustained release mechanism designed to deliver key components to yeast throughout fermentation. The sustained release system was developed to simulate multiple powder additions. MEC-TR was produced using a stainless steel die with 1-inch (2.5 cm) diameter, 0.25-inch (6 mm) height, and compressed using a bench mounted H-frame utility hydraulic press brand (DAKE, a Division of JSJ Corporation, Grand Haven, Mich.) with flat ram nose. Each MEC-TR tablet weighed about 4g.

Figure 1:
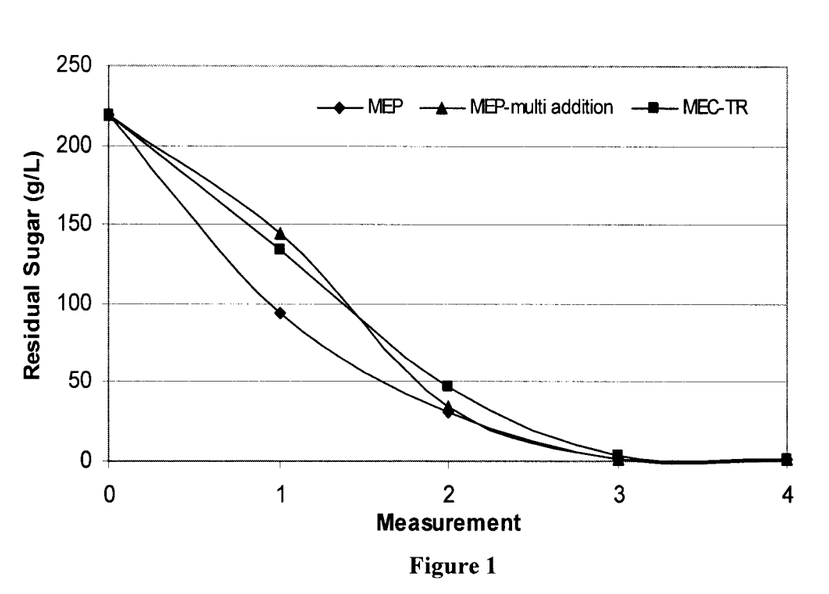
FIG. 1 is a graph which illustrates the effect of sustained release functionally on fermentation rate of Chardonnay juice in Example 1.

MEC-TR was added to the fermentation vessel at 4 g/3 L at the onset of fermentation. MEP was added in powder form to the fermentation vessel at 4 g/3 L at the onset of fermentation. MEP-multi addition was added in powder form to the fermentation vessel in two aliquots (2 g/3 L initially and 2 g/3 L after 48-72 hours). All treatments were inoculated with *Saccharomyces cerevisiae* (Ruby.ferm) yeast (Chr Hansen, Denmark) and fermented at 72° F. (22° C.) in 3 L glass vessels until dryness (<2 g/L residual sugar). The fermentation was shown to proceed very quickly, when nutrients were added in powder form. Nutrient addition via sustained release mechanism supplied the microbes with needed nutrients at key phases during the fermentation. These fermentations began more slowly but completed fermentation at the same rate. The juice was very nutrient rich; therefore, all fermentations proceeded faster than typical fermentations. Fermentation curves are shown in FIG. 1.

EXAMPLE 2

The objective of this example was to compare the fermentation profiles between MEP (Gusmer Enterprises, Fresno, Calif.), MEC-TR, and a competitor product. The competitor product in Example 2 was a combination of diammonium phosphate (American Tartaric Products, Larchmont, N.Y.) and SUPERFOOD (Sensient Technologies, Milwaukee, Wis.), a complex yeast nutrient blend containing yeast hulls, yeast extract, diammonium phosphate, vitamins and minerals. The competitor products (diammonium phosphate and SUPERFOOD) do not have sustained release functionality; therefore, multiple administrations were performed when comparing these products to products containing sustained release systems. The combination of diammonium phosphate and SUPERFOOD was selected as a comparison because those products are customarily used by RH Phillips for nutrient additions.

Syrah grapes (RH Phillips, Woodland, Calif.) were harvested and separated into three commercial winery tanks each containing 16 tons of fruit with appropriate water additions to reduce Brix. MEP, MEC-TR, and DAP/SUPERFOOD products were utilized in this experiment.

Active ingredients and excipients were blended thoroughly before being compressed into tablets and then added to the juice as MEC-TR. MEC-TR contains the sustained release mechanism designed to deliver key components to yeast throughout the fermentation. The sustained release system was developed to simulate multiple powder additions. The MEC-TR tablets were produced using a stainless steel, concave, bevel-edge die with about 1.5-inch (4 cm) diameter, 0.69-inch (1.75 cm) height, and compressed using a Stokes R4 press. Each MEC-TR tablet weighed 20-26 g.

Figure 2:
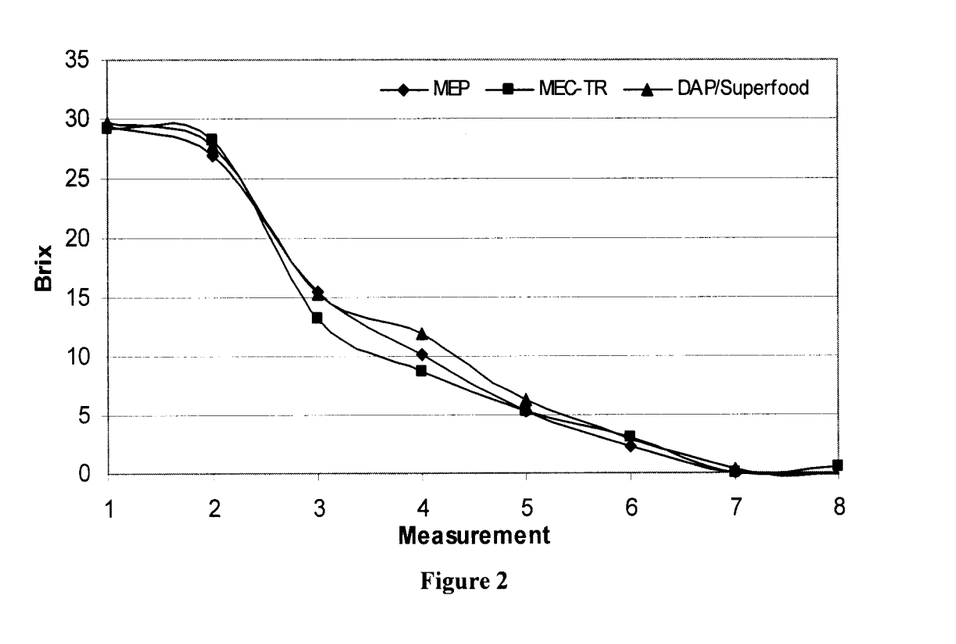
FIG. 2 is a graph which illustrates the effect of Micro-Essentials Powder, Micro-Essentials Complete-Time Release, and Competitor products on fermentation rate of Syrah grapes in Example 2.

MEC-TR was added to the fermentation tank at 5 lbs/1000 G at the onset of fermentation. MEP was added in powder form to the fermentation tank in two aliquots (2 lbs/1000 G initially and 2 lbs/1000 G after 48-72 hours). The DAP/SUPERFOOD combination was added in powder form to the fermentation tank in two aliquots (1 lb DAP/1000 G with 1 lb SUPERFOOD/1000 G initially and 1 lb DAP/1000 G with 1 lb SUPERFOOD/1000 G after 48-72 hours). All treatments were inoculated with *Saccharomyces cerevisiae* (D254) yeast and fermented initially at 18° C. After 48-72 hours ferment temperature was increased to 75° F. (24° C.) and fermented until dryness (<2 g/L residual sugar). MEP exhibited the same performance profile as MEC-TR illustrating the value of sustained release functionality in a controlled fermentation. Both MEP and MEC-TR performed equally well compared to the DAP/SUPERFOOD combination. Fermentation curves are shown in FIG. 2.

EXAMPLE 3

The objective of this example was to determine the performance of a commercial scale fermentation comparing MEC-TR and a competitor product. The competitor product of Example 3 was a combination of diammonium phosphate (American Tartaric Products, Larchmont, N.Y.) and Fermaid K (Lallemand, Montreal, Quebec). Fermaid K is a complete yeast nutrient that supplies diammonium phosphate, free amino acids, sterols, unsaturated fatty acids, key nutrients (magnesium sulfate, thiamin, folic acid, niacin, biotin, calcium pantothenate) and inactive yeast. The competitor products (diammonium phosphate and Fermaid K) do not have sustained release functionality; therefore, multiple administrations were performed when comparing these products to products containing sustained release systems. The combination of diammonium phosphate and Fermaid K was selected as a comparison because those products are customarily used by Stellenzicht (Stellenbosch, South Africa) for nutrient additions.

Cabernet franc grapes (Stellenzicht) were harvested and separated into two commercial winery tanks each containing approximately 14 tons of fruit. MEC-TR and DAP/Fermaid K were utilized in this experiment.

Active ingredients and excipients were blended thoroughly before being compressed into tablets and then added to the juice as MEC-TR. MEC-TR contains the sustained release mechanism designed to deliver key components to yeast throughout the fermentation. The sustained release system was developed to simulate multiple powder additions. The MEC-TR tablets were produced using a stainless steel, concave, bevel-edge die with 1.5-inch (4 cm) diameter, 0.69-inch (1.75 cm) height, and compressed using a Stokes R4 press. Each MEC-TR tablet weighed 20-26 g.

Figure 3:
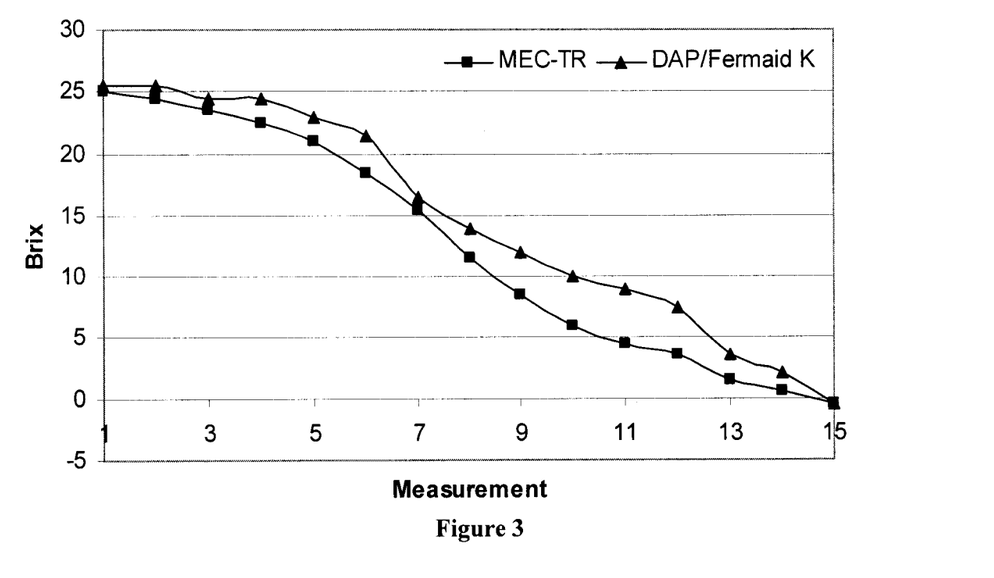
FIG. 3 is a graph which illustrates the effect of Micro-Essentials Complete-Time Release compared to a Competitor product on fermentation rate of Cabernet Franc grapes in Example 3.

MEC-TR was added to the fermentation tank at 66 g/hL at the onset of fermentation. The DAP/Fermaid K combination was added in powder form to the fermentation tank in two aliquots (20 g DAP/hL with 13 g Fermaid K/hL initially and 20 g DAP/hL with 13 g Fermaid K/hL after 48-72 hours). All treatments were inoculated with *Saccharomyces cerevisiae* (NT50) yeast (Anchor Yeast, Cape Town, South Africa) and fermented in the range of 64-75° F. (18-24° C.) until dryness (<2 g/L residual sugar). MEC-TR exhibited a controlled fermentation that progressed slightly quicker than the competitor product. Fermentation curves are shown in FIG. 3.

EXAMPLE 4

The objective of this example is to evaluate the release rate of ammonia via the sustained release mechanism of MEB-TR.

Cabernet sauvignon juice concentrate are diluted to 15 Brix and separated into three 1 L treatment vessels. The treatments include Powder without Time Release Ingredients ("P-noTR"), Powder with Time Release Ingredients ("P-TR") and MEB-TR products.

Active ingredients and excipients are blended thoroughly before being compressed into tablets and then added to the juice as MEB-TR. Ingredients for P-noTR and P-TR treatments were blended thoroughly before being added to the juice in powder form. MEB-TR is produced using a stainless steel, concave, bevel-edge die with 1.5-inch (4 cm) diameter, 0.69-inch (1.75 cm) height, and compressed using a Stokes R4 press. Each MEB-TR tablet is expected to weigh 20-26 g. P-noTR does not have sustained release functionality. P-TR and MEB-TR both contain sustained release systems.

Products containing the sustained release mechanism are expected to show a 20-30% release of ammonia within the first few hours with a continual release of remaining ammonia over 72 hours. Products without the sustained release mechanism are expected to show complete ammonia release within the first few hours.

EXAMPLE 5

The objective of this example is to evaluate the release rate of zinc via the sustained release mechanism of MEB-TR.

Cabernet sauvignon juice concentrate is diluted to 15 Brix and separated into three 1 L treatment vessels. The treatments include Powder without Time Release Ingredients ("P-noTR"), Powder with Time Release Ingredients ("P-TR") and MEB-TR products.

Active ingredients and excipients are blended thoroughly before being compressed into tablets and then added to the juice as MEB-TR. Ingredients for P-noTR and P-TR treatments were blended thoroughly before being added to the juice in powder form. MEB-TR is produced using a stainless steel, concave, bevel-edge die with 1.5-inch (4 cm) diameter, 0.69-inch (1.75 cm) height, and compressed using a Stokes R4 press. Each MEB-TR tablet is expected to weight 20-26 g. P-noTR does not have sustained release functionality. P-TR and MEB-TR both contain sustained release systems.

Products containing the sustained release mechanism are expected to show a 20-30% release of zinc within the first few hours with a continual release of remaining zinc over 72 hours. Products without the sustained release mechanism are expected to show complete zinc release within the first few hours.

EXAMPLE 6

The objective of this example is to monitor the effect of sustained release lysozyme and its ability to reduce malolactic bacteria.

Lysozyme is used by winemakers to control the growth of gram-positive spoilage bacteria, which can create sluggish fermentations and increase volatile acidity. Lysozyme controls various aspects of malolactic fermentation and stabilizes wines after alcoholic fermentation.

Chardonnay juice concentrate is diluted to 15 Brix, adjusted to pH 3.5, and inoculated with Viniflora Oenos (Chr Hansen, Denmark) malolactic bacteria. Three days following inoculation, juice is separated into three treatments vessels.

Active ingredients and excipients are blended thoroughly before being compressed into tablets. The Lysozyme-TR contains the sustained release mechanism and is utilized for this experiment. Lysozyme-TR is produced using a stainless steel, concave, bevel-edge die with 1.5-inch (4 cm) diameter, 0.69-inch (1.75 cm) height, and compressed using a STOKES R4 press. Each Lysozyme-TR tablet is expected to weigh 20-26 g.

Wallerstein Differential media is used to monitor malolactic bacteria growth. The addition of Lysozyme to juice is expected to control the development of indigenous bacteria and prevent the occurrence of premature malolactic fermentation. The addition of Lysozyme to wine is expected to reduce the bacterial population and lessen the formation of volatile acidity.

EXAMPLE 7

The objective of this example is to evaluate internal applications of the sustained release mechanism when incorporated into the extruded material.

Extrusion Trials—Sustained release components are blended and extruded using a Kitchen Aid mixer with pasta attachment. Several water soluble sustained release components are evaluated including various alginates and gelatins. Extruded material is dried in an oven prior to producing pellets. Pellets are placed into Cabernet sauvignon wine for evaluation. After 24 hours in wine, the sample exhibits good properties and holds together well.

EXAMPLE 8

The objective of this example is to evaluate external applications of the sustained release mechanism when applied to an extruded material.

Coating Trials—Sustained release components are blended and used to coat extruded pellets. Coatings are applied using a rotary evaporator. Pellets are coated with various non-water soluble sustained release agents including shellacs, waxes, and zeins. Pellets are placed into Chardonnay and Cabernet sauvignon wines for evaluation. The use of coatings is expected to increase release time compared to control samples.

EXAMPLE 9

The objective of this example is to evaluate internal applications of the sustained release mechanism when incorporated into a tablet product.

Gelatin Trials—Active ingredients and excipients are blended thoroughly before being compressed into tablets. The sustained release tablets are produced using a stainless steel, concave, bevel-edge die with 1.5-inch (4 cm) diameter, 0.69-inch (1.75 cm) height, and compressed using a STOKES R4 press. Each sustained release tablet is expected to weigh 20-26 g. Several types of gelatin are trialed as a component of the sustained release mechanism. The use of gelatins is expected to increase release time compared to control samples.

EXAMPLE 10

The objective of this example is to compare the fermentation profiles between MEP, MEC-TR, and other commercially available products.

Beer and other fermented beverages can benefit from sustained release additives. Active ingredients and excipients are blended thoroughly before being compressed into tablets and then added to the fermentation. The sustained release tablets are produced using a stainless steel, concave, bevel-edge die with 1.5-inch (4 cm) diameter, 0.69-inch (1.75 cm) height, and compressed using a STOKES R4 press. Each sustained release tablet is expected to weigh 20-26 g. After products are added, treatments are inoculated with yeast and fermented. MEP and commercial products will be added in multiple aliquots throughout fermentation. MEC-TR will be added one time at the beginning of fermentation. Sustained release functionality is expected to provide more reliable fermentations for beer and other fermented beverages.

EXAMPLE 11

The objective of this example is to keep fermentations from becoming nutrient depleted during continuous fermentations. Since fermentation is a critical step in a distillery, the biofuels industry can also benefit from sustained release nutrients. Fuel alcohol manufacturers often use a continuous fermentation system in which the yeast is recycled and re-added to the fermentor to provide additional catalytic activity and increase the production rate (Ingledew, W. M., 2003). With these continuous cultures, nutrients must be added multiple times to ensure proper yeast nutrition.

Active ingredients and excipients are blended thoroughly before being compressed into tablets and then added to the fermentation. The sustained release tablets are produced using a stainless steel, concave, bevel-edge die with 1.5-inch (4 cm) diameter, 0.69-inch (1.75 cm) height, and compressed using a STOKES R4 press. Each sustained release tablet is expected to weigh 20-26 g.

Since many biofuels fermentations are continuous, the sustained release tablets are added when nutrient levels become depleted. The sustained release nutrients are expected to provide a consistent level of nutrition in the fermentors and establish more constant alcohol production rates.

EXAMPLE 12

The objective of this example is to show the effect of using Natamycin as an anti-microbial agent in controlling wine spoilage organisms, particularly *Brettanomyces*.

Natamycin is used worldwide as a natural preservative primarily for treatment of cheese and dried sausages; however, research indicates that natamycin is effective in controlling yeast spoilage of wine post-fermentation. Natamycin is legal in some countries for bottling of semi-sweet wine to prevent re-fermentation in the bottle.

Active ingredients and excipients are blended thoroughly before being compressed into tablets. Natamycin-TR tablets with sustained release mechanisms incorporated into the tablet are produced using a stainless steel, concave, bevel-edge die with 1.5-inch (4 cm) diameter, 0.69-inch (1.75 cm) height, and compressed using a STOKES R4 press. Each Natamycin-TR tablet is expected to weigh 20-26 g.

Natamycin-TR tablets are added to juice or wine to improve microbiological stability in tanks, bottles, and barrels. Microbiological stability is a major issue in low acid products with high levels of fermentable sugar. Natamycin is expected to protect against re-fermentation and spoilage.

EXAMPLE 13

Sulfur dioxide is widely used in juices, wine, and many foodstuffs as a chemical antioxidant and microbial inhibitor.

Active ingredients and excipients are blended thoroughly before being compressed into tablets. Sulfur dioxide ($SO_2$-TR) tablets with sustained release mechanisms incorporated into the tablet are produced using a stainless steel, concave, bevel-edge die with 1.5-inch (4 cm) diameter, 0.69-inch (1.75 cm) height, and compressed using a Stokes R4 press. Each $SO_2$-TR tablet is expected to weight 20-26 g.

$SO_2$-TR tablets are added to juice or wine to inhibit oxidation, to kill and inhibit development of microorganisms, and to inhibit phenoloxidase activity. Sulfur dioxide added via sustained release systems is expected to protect against spoilage and oxidation.

It is understood that the invention is not confined to the particular construction and arrangement of parts herein illustrated and described, but embraces such modified forms thereof as come within the scope of the claims following the Bibliography.

BIBLIOGRAPHY

Agenbach, W. A. 1977. A study of must nitrogen content in relation to incomplete fermentations, yeast production and fermentation activity. In: Proceedings of the South African Society for Enology and Viticulture, Cape Town, pp 66-88.

Alfenore, S., C. Molina-Jouve, and S. E. Guillouet. 2002. Improving ethanol production and viability of *Saccharomyces cerevisiae* by a vitamin feeding strategy during fed-batch process. Appl. Microbiol. Biotechnol. 60:67-72.

Butzke, C. E. 1998. Survey of yeast assimilable nitrogen status in musts from California, Oregon, and Washington. Am. J. Enol. Vitic. 49:220-224.

Chaney, D., S. Rodriguez, K. Fugelsang, and R. Thornton. 2006. Managing high-density commercial scale wine fermentations. J. Appl. Micro. 100:689-698.

Chaudhari, D. 2004. Controlled drug delivery systems. Literature Seminar—University of Alabama.

Ingledew, W. M. 2003. Continuous fermentation in the fuel alcohol industry: How does the technology affect yeast? In: The Alcohol Textbook—A Reference for the Beverage, Fuel and Industrial Alcohol Industries. K. A. Jacques, T. P. Lyons, and D. R. Kelsall, eds. 4$^{th}$ Edition. Nottingham University Press.

Ingledew, W. M. and R. Kunkee. 1985. Factors influencing sluggish fermentations of grape juice. Am. J. Enol. Vitic. 36:65-76.

Julien, A., J. L. Roustan, L. Dulau, and J. M. Sablayrolles. 2000. Comparison of nitrogen and oxygen demands of enological yeasts: technological consequences. Am. J. Enol. Vitic. 51:215-222.

Kaparissides, C., S. Alexandridou, K. Kotti, and S. Chaitidou. 2006. Recent advances in novel drug delivery systems. AZojono—Journal of Nanotechnology Online. 2:1-11.

Kellerby, Joe D., U.S. Pat. No. 5,472,955, entitled "Insecticide Mixture for Ear Tags, issued Dec. 5, 1995.

Lachman, L., H. A. Lieberman, and J. L. Kanig. 1986. The Theory of Practice of Industrial Pharmacy, 3$^{rd}$ Ed., Lea & Febiger, Philadelphia.

Lachman, L., H. A. Lieberman, and J. L. Kanig. 1971. The Theory of Practice of Industrial Pharmacy, 3$^{rd}$ Ed., Lea & Febiger, Philadelphia.

Lakkis, J. M. 2007. Encapsulation and Controlled Release Technologies in Food Systems. Blackwell Publishing Professional, Ames, Iowa (Don't have this reference—estimated due date is July 2007).

Manginot, C., J. L. Roustan, J. M. Sablayrolles. 1998. Nitrogen demand of different yeast strains during alcoholic fermentation. Importance of the stationary phase. Enzyme and Microbial Technology. 23:511-517.

Ough, C. F., M. Davenport, and K. Joseph. 1989. Effects of certain vitamins on growth and fermentation rate of several commercial active dry wine yeasts. Am. J. Enol. Vitic. 40:208-213.

Porter, S. 1990. Chapter 89. In: Remington's Pharmaceutical Sciences. 18$^{th}$ Ed. Mack Publishing Co. Easton, Pa.

Sablayrolles, J. M., C. Dubois, C. Manginot, J. L. Roustan, and P. Barre. 1996. Effectiveness of combined ammoniacal nitrogen and oxygen additions for completion of sluggish and stuck wine fermentations. Journal of Fermentation and Bioengineering. 82:377-381.

Shelke, K. 2005. The hidden ingredients: encapsulation technologies protect key ingredients and deliver them at just the right moment. (Encapsulation)(Micro-encapsulation). Food Processing—published online Jul. 1, 2005.

Tyle, P. 1990. Chapter 10. In: Specialized drug delivery systems, manufacturing and production technology. P. K. Wilkinson and F. S. Hom, eds. Marcel Dekker, New York.

U.S. Department of Health and Human Services, Food and Drug Administration, Center for Drug Evaluation and Research (CDER). 1997. Guidance for Industry—SUPAC-IR: Immediate Release Solid Oral Dosage Forms. Manufacturing Equipment Addendum.

Vogelson, C. T. 2001. Advances in drug delivery systems. Modern Drug Discovery. 4(4):49-50, 52.

What is claimed is:

1. A composition for the sustained release of additives in a fermentation fluid comprising: a gelling agent, at least one additive, a calcium source and a binder, wherein the gelling agent is selected from the group consisting of sodium alginate, potassium alginate, calcium alginate, magnesium alginate, ammonium alginate, and triethanolamine alginate, wherein the at least one additive includes a yeast-derived additive, and wherein the gelling agent and the binder are present in amounts effective to allow the sustained release of the at least one additive in the fermentation fluid for a period of time up to 96 hours,
   wherein the gelling agent is selected from the group consisting of sodium alginate, potassium alginate, calcium alginate, magnesium alginate, ammonium alginate, and triethanolamine aiginate;
   wherein the calcium source is selected from the group consisting of calcium chloride, calcium citrate, calcium phosphate, calcium carbonate, calcium lactate, calcium aspartate, calcium stearate, tri-calcium and calcium sulfate;
   wherein a calcium source is present in an amount effective to allow the sustained release of the additive in the fermentation fluid for a period of at least 12 hours.

2. The composition of claim 1 wherein the gelling agent and the binder are present in amounts sufficient to allow the sustained release of the additive in the fermentation fluid for a period of time up to 72 hours.

3. The composition of claim 1 wherein the fermentation fluid is selected from the group consisting of juice, beverages, foodstuffs, and biofuels production.

4. The composition of claim 1 wherein the gelling agent is sodium alginate.

5. The composition of claim 1 where the gelling agent is present in an amount ranging from 0% to 20% by weight.

6. The composition of claim 1 where the gelling agent is present in an amount ranging from 2% to 8% by weight.

7. A composition for the sustained release of additives in a fermentation fluid comprising: a gelling agent, at least one additive, a calcium source, and a binder, wherein the at least one additive includes a yeast-derived additive, wherein the gelling agent and the binder are present in amounts effective to allow the sustained release of the at least one additive in the fermentation fluid for a period of time up to 96 hours, and wherein the calcium source is present in an amount effective to allow the sustained release of the additive in the fermentation fluid for a period of at least 12 hours.

8. The composition of claim 7 wherein the calcium source is selected from the group consisting of calcium chloride, calcium citrate, calcium phosphate, calcium carbonate, calcium lactate, calcium aspartate, calcium stearate, and calcium sulfate.

9. The composition of claim 7 wherein the calcium source is tri-calcium citrate.

10. The composition of claim 1 wherein the binder is selected from the group consisting of adsorbents, fillers, antioxidants, buffering agents, colorants, flavorants, sweetening agents, tableting agents, tablet anti-adherents, lubricants, tablet binders, diluents, tablet direct compression excipients, tablet disintegrants, tablet glidants, polishing agents, magnesium stearate, calcium stearate, zinc stearate, powdered stearic acid, hydrogenated vegetable oils, talc, polyethylene glycol, mineral oil, an FD&C color, modified cellulose, lactose, polyethylene glycol, colloidal silicon dioxide, sodium lauryl sulfate, quaternary ammonium salts, mannitol, sodium chloride, sodium sulfate, sodium phosphate, magnesium chloride, magnesium sulfate, magnesium phosphate, microcrystalline cellulose, sodium starch glycolate, lactose, sucrose, glucose, calcium carbonate, colloidal anhydrous silica, polyethylene glycols, waxes, hydrogenated castor oil, starch, and polyvinyl pyrrolidone.

11. The composition of claim 1 wherein the binder is microcrystalline cellulose.

12. The composition of claim 1 wherein the additive further comprises a nitrogen source independent of the yeast-derived additive present in an amount ranging from 35% to 75% by weight.

13. The composition of claim 12 wherein the nitrogen source is selected from the group consisting of ammonium, ammonia gas, diammonium phosphate, diammonium sulfate, nitrite, nitrate, proteins, amino acids, and urea.

14. The composition of claim 12 wherein the nitrogen source is diammonium phosphate.

15. The composition of claim 1 wherein the yeast-derived additive comprises a yeast extract.

16. The composition of claim 1 wherein the at least one additive further comprises a source of nutritionally effective amounts of vitamins and minerals independent of the yeast-derived additive.

17. The composition of claim 1 present in the form of a tablet selected from a size effective to sustain the release of the additive in the fermentation fluid for a period of at least 12 hours.

18. A sustained release nutrient system for a fermentation fluid comprising a gelling agent that includes alginate, a binder that includes a calcium source, and additives that include a yeast-derived additive and a source of nutritionally effective amounts of vitamins and minerals independent of the yeast-derived additive, wherein the gelling agent and the binder are present in effective amounts sufficient to allow the sustained release of the additives in the fermentation fluid for a period of time up to 96 hours.

19. The sustained release nutrient system of claim 18 wherein the additives further comprise a nitrogen source independent of the yeast-derived additive, the source of vitamins and minerals, and the calcium source.

20. The sustained release nutrient system of claim 18 wherein the calcium source is tri-calcium citrate.

21. The composition of claim 1 wherein the yeast-derived additive comprises yeast hull.

22. The sustained release nutrient system of claim 18 wherein the additives further comprise one or more enzymes.

23. The sustained release nutrient system of claim 22 wherein the one or more enzymes comprise lysozyme.

24. The sustained release nutrient system of claim 18 wherein the additives further comprise one or more preservatives.

25. The sustained release nutrient system of claim 24 wherein the one or more preservatives comprise sulfur dioxide.

26. The sustained release nutrient system of claim 24 wherein the one or more preservatives comprise natamycin.

27. The sustained release nutrient system of claim 18 wherein the additives include a living organism selected from the group consisting of a bacterium and a yeast.

28. The sustained release nutrient system of claim 18 wherein the yeast-derived additive comprises yeast hull.

* * * * *